United States Patent [19]
Scott et al.

[11] Patent Number: 5,932,763
[45] Date of Patent: Aug. 3, 1999

[54] INHIBITION OF MATRIX METALLOPROTEASES BY 2-(ω-AROLALKYL)-4-BIARYL-4-OXOBUTYRIC ACIDS

[75] Inventors: William J. Scott, Guilford; Margaret A. Popp, Branford, both of Conn.; David S. Hartsough, Stoneham, Mass.

[73] Assignee: Bayer Corporation, Pittsburgh, Pa.

[21] Appl. No.: 08/856,695

[22] Filed: May 15, 1997

[51] Int. Cl.$^6$ ..................... C07C 59/76
[52] U.S. Cl. .............. 562/460; 562/434; 562/429; 514/561; 514/568; 514/569
[58] Field of Search .................. 562/460, 429, 562/434

[56] References Cited

U.S. PATENT DOCUMENTS 4,337,267  6/1982  Eistetter et al. .

FOREIGN PATENT DOCUMENTS

| 0180290 | 5/1986 | European Pat. Off. ........ C07C 59/88 |
| 0496555 | 7/1992 | European Pat. Off. .......... C09D 5/08 |
| 9615096 | 5/1996 | WIPO .............................. C07C 59/88 |

*Primary Examiner*—Paul J. Killos

[57] ABSTRACT

The present invention provides pharmaceutical compositions and methods for treating certain conditions comprising administering an amount of a compound or composition of the invention which is effective to inhibit the activity of at least one matrix metalloprotease, resulting in achievement of the desired effect. The compounds of the present invention are of the generalized formula

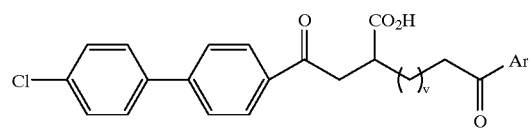

where v is 1, 2, 3 or 4 and Ar represents a substituted aromatic moiety. These compounds are useful for inhibiting matrix metalloproteases and, therefore, combating conditions to which MMP's contribute, such as osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system, tumor metastasis or degenerative cartilage loss following traumatic joint injury, and coronary thrombosis from atherosclerotic plaque rupture. The present invention also provides pharmaceutical compositions and methods for treating such conditions.

12 Claims, No Drawings

5,932,763

INHIBITION OF MATRIX METALLOPROTEASES BY 2-(ω-AROLALKYL)-4-BIARYL-4-OXOBUTYRIC ACIDS

BACKGROUND OF THE INVENTION

1. Field of the Invention

This invention relates to enzyme inhibitors, and more particularly, to novel 2-(ω-aryoylalkyl)-4-biaryl-4-oxobutyric acid compounds or derivatives thereof useful for inhibiting matrix metalloproteases.

2. Description of the Related Art

The matrix metalloproteases (a.k.a. matrix metalloendoproteinases or MMPs) are a family of zinc endoproteinases which include, but are not limited to, interstitial collagenase (a.k.a. MMP-1), stromelysin (a.k.a. proteoglycanase, transin, or MMP-3), gelatinase A (a.k.a. 72 kDa-gelatinase or MMP-2) and gelatinase B (a.k.a. 95 kDa-gelatinase or MMP-9). These MMPs are secreted by a variety of cells including fibroblasts and chondrocytes, along with natural proteinaceous inhibitors known as TIMPs (Tissue Inhibitor of MetalloProteinase).

All of these MMPs are capable of destroying a variety of connective tissue components of articular cartilage or basement membranes. Each MMP is secreted as an inactive proenzyme which must be cleaved in a subsequent step before it is able to exert its own proteolytic activity. In addition to the matrix destroying effect, certain of these MMPs such as MMP-3 have been implemented as the in vivo activator for other MMPs, such as MMP-1 and MMP-9 (Ito, et al., Arch. Biochem. Biophys. 267, 211, 1988; Ogata, et al., J. Biol. Chem., 267, 3581, 1992). Thus, a cascade of proteolytic activity can be initiated by an excess of MMP-3. It follows that specific MMP-3 inhibitors should limit the activity of other MMPs that are not directly inhibited by such inhibitors.

It has also been reported that MMP-3 can cleave and thereby inactivate the endogenous inhibitors of other proteinases such as elastase (Winyard, et al., FEBS Letts. 279, 91, 1991). Inhibitors of MMP-3 could thus influence the activity of other destructive proteinases by modifying the level of their endogenous inhibitors.

A number of diseases are thought to be mediated by excess or undesired matrix-destroying metalloprotease activity or by an imbalance in the ratio of the MMPs to the TIMPs. These include: a) osteoarthritis (Woessner, et al., J. Biol.Chem., 259, 3633, 1984; Phadke, J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res., 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Burns, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

The need for new therapies is especially important in the case of arthritic diseases. The primary disabling effect of osteoarthritis (OA), rheumatoid arthritis (RA) and septic arthritis is the progressive loss of articular cartilage and thereby normal joint function. No marketed pharmaceutical agent is able to prevent or slow this cartilage loss, although nonsteroidal anti-inflammatory drugs (NSAIDs) have been given to control pain and swelling. The end result of these diseases is total loss of joint function which is only treatable by joint replacement surgery. MMP inhibitors are expected to halt or reverse the progression of cartilage loss and obviate or delay surgical intervention.

Proteases are critical elements at several stages in the progression of metastatic cancer. In this process, the proteolytic degradation of structural protein in the basal membrane allows for expansion of a tumor in the primary site, evasion from this site, as well as homing and invasion in distant, secondary sites. Also, tumor induced angiogenesis is required for tumor growth and is dependent on proteolytic tissue remodeling. Transfection experiments with various types of proteases have shown that the matrix metalloproteases, in particular gelatinases A and B (MMP-2 and MMP-9, respectively) play a dominant role in these processes. For an overview of this field, see: Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see: DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis, or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al,. EP 276436; and Myers, et al., EP 520573 A1). The preferred compounds of these patents have peptide backbones with a zinc complexing group (hydroxamic acid, thiol, carboxylic acid or phosphorous based acid) at one end and a variety of sidechains, both those found in the natural amino acids as well as those with more novel functional groups. Such small peptides are often poorly absorbed, exhibiting low oral bioavailability. They are also subject to rapid proteolytic metabolism, thus having short half lives. As an example, batimastat, a compound described in Brown, et al., WO-9321942 A2, can only be given intra peritoneally.

Certain 3-biphenoylpropanoic and 4-biaroylbutanoic acids are described in the literature as anti-inflammatory, anti-platelet aggregation, anti-phlogistic, anti-proliferative, hypolipidemic, antirheumatic, analgesic, and hypocholesterolemic agents. In none of these examples is a reference made to MMP inhibition as a mechanism for the claimed therapeutic effect. Certain related compounds are also used as intermediates in the preparation of liquid crystals.

Specifically, Tomcufcik, et al., U.S. Pat. No. 3,784,701 claims certain substituted benzoylpropionic acids to treat inflammation and pain. These compounds include 3-biphenoylpropanoic acid (a.k.a. fenbufen) shown below.

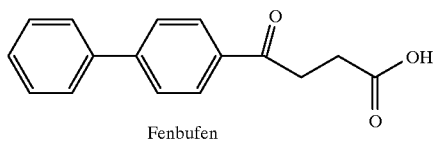

Fenbufen

Child, et al., J. Pharm. Sci., 66, 466, 1977 describes structure-activity relationships of several analogs of fenbufen. These include several compounds in which the biphenyl ring system is substituted or the propanoic acid portion is substituted with phenyl, halogen, hydroxyl or methyl, or the carboxylic acid or carbonyl functions are converted to a variety of derivatives. No compounds are described which contain a 4'-substituted biphenyl and a substituted propanoic acid portion combined in one molecule. The phenyl (compounds XLIX and LXXVII) and methyl (compound XLVII) substituted compounds shown below were described as inactive.

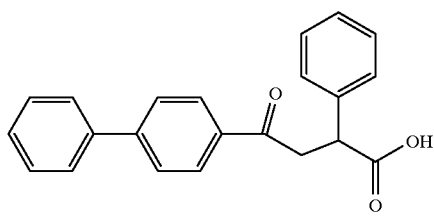

XLIX

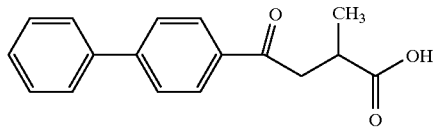

XLVII

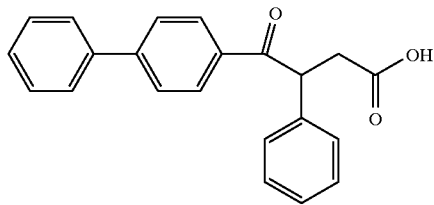

LXXVII

Kameo, et al., Chem. Pharm. Bull., 36, 2050, 1988 and Tomizawa, et al., JP Pat. No. 62132825 A2 describe certain substituted 3-biphenoylpropionic acid derivatives and analogs thereof including the following, wherein X=H, 4'-Br, 4'-Cl, 4'-CH$_3$, or 2'-Br. Various compounds with other substituents on the propionic acid portion are described, but they do not contain biphenyl residues.

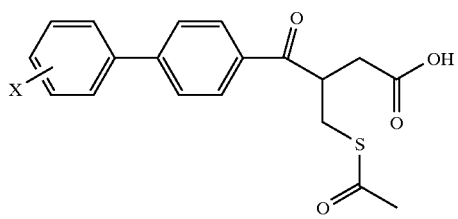

Cousse, et al., Eur. J. Med. Chem., 22, 45, 1987 describe the following methyl and methylene substituted 3-biphenoylpropanoic and -propenoic acids, wherein X=H, Cl, Br, CH$_3$O, F, or NH$_2$.

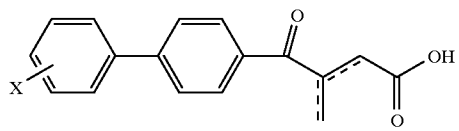

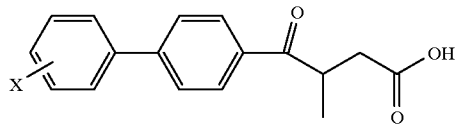

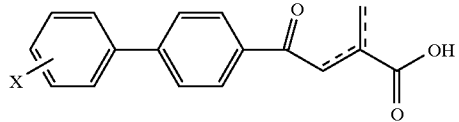

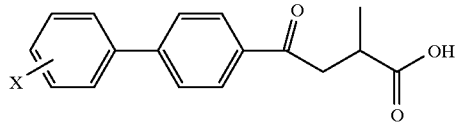

The corresponding compounds in which the carbonyl is replaced with either CH$_2$OH or CH$_2$ are also described. Nichl, et al. DE Pat. No. 1957750 also describes certain of the above methylene substituted biphenoylpropanoic acids.

El-Hashash, et al., Revue Roum. Chim. 23, 1581, 1978 describe products derived from β-aroylacrylic acid epoxides including the following biphenyl compound (no compounds substituted on the biphenyl portion are described):

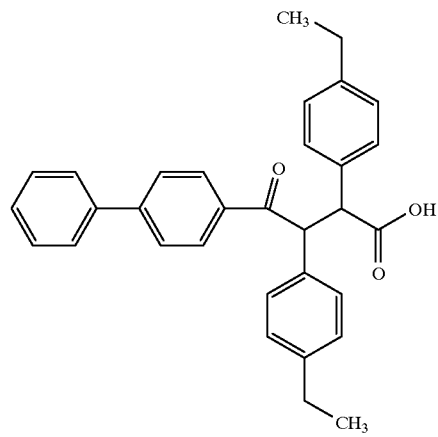

Kitamura, et al., JP patent 60209539 describes certain biphenyl compounds used as intermediates for the production of liquid crystals including the following:

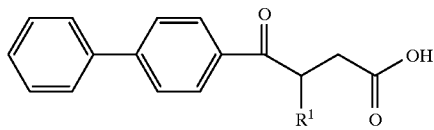

wherein R¹ is an alkyl of 1–10 carbons. The biphenyl is not substituted in these intermediates.

Thyes, et al., DE Pat. No. 2854475 uses the following compound as an intermediate (the biphenyl group is not substituted):

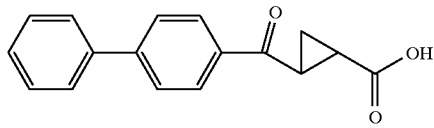

Sammour, et al., Egypt. J. Chem. 15, 311, 1972 and Couquelet, et al., Bull. Soc. Chim. Fr. 9, 3196, 1971 describe certain dialkylamino substituted biphenoylpropanoic acids including the following:

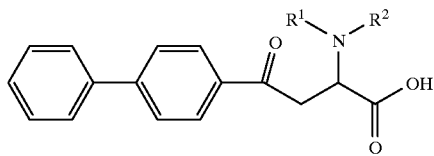

wherein R¹, R²=alkyl, benzyl, H, or, together with the nitrogen, morpholinyl. In no case is the biphenyl group substituted.

Others have disclosed a series of biphenyl-containing carboxylic acids, illustrated by the compound shown below, which inhibit neural endopeptidase (NEP 24.11), a membrane-bound zinc metalloprotease (Stanton, et al., Bioorg. Med. Chem. Lett. 4, 539, 1994; DeLombaert, et al., Bioorg. Med. Chem. Lett. 4, 2715, 1994; DeLombaert, et al., Bioorg. Med. Chem. Lett. 5, 145, 1995; DeLombaert, et al., Bioorg. Med. Chem. Lett. 5, 151, 1995).

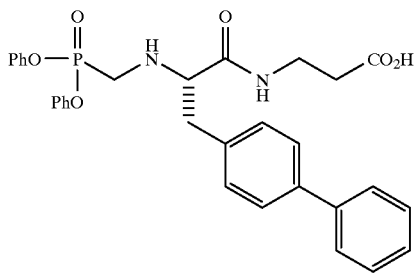

It has been reported that N-carboxyalkyl derivatives containing a biphenylethylglycine, illustrated by the compound shown below, are inhibitors of stromelysin-1 (MMP-3), 72 kDa gelatinase (MMP-2) and collagenase (Durette, et al., WO-9529689).

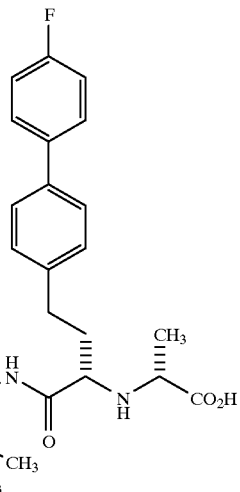

It would be desirable to have effective MMP inhibitors which possess improved bioavailability and biological stability relative to the peptide-based compounds of the prior art, and which can be optimized for use against particular target MMPs. Such compounds are the subject of the present application.

The development of efficacious MMP inhibitors would afford new therapies for diseases mediated by the presence of, or an excess of MMP activity, including osteoarthritis, rheumatoid arthritis, septic artritis, tumor metastasis, periodontal diseases, corneal ulcerations, and proteinuria. Several inhibitors of MMPs have been described in the literature, including thiols (Beszant, et al., J. Med. Chem. 36, 4030, 1993), hydroxamic acids (Wahl, et al. Bioorg. Med. Chem. Lett. 5, 349, 1995; Conway, et al. J. Exp. Med. 182, 449, 1995; Porter, et al., Bioorg. Med. Chem. Lett. 4, 2741, 1994; Tomczuk, et al., Bioorg. Med. Chem. Lett. 5, 343, 1995; Castelhano, et al., Bioorg. Med. Chem. Lett. 5, 1415, 1995), phosphorous-based acids (Bird, et al. J. Med. Chem. 37, 158, 1994; Morphy, et al., Bioorg. Med. Chem. Lett. 4, 2747, 1994; Kortylewicz, et al., J. Med. Chem. 33, 263, 1990), and carboxylic acids (Chapman, et al. J. Med. Chem. 36, 4293, 1993; Brown, et al. J. Med. Chem. 37, 674, 1994; Morphy, et al., Bioorg. Med. Chem. Lett. 4, 2747, 1994; Stack, et al., Arch. Biochem. Biophys. 287, 240, 1991; Ye, et al., J. Med. Chem. 37, 206, 1994; Grobelny, et al., Biochemistry 24, 6145, 1985; Mookhtiar, et al., Biochemistry 27, 4299, 1988). However, these inhibitors generally contain peptidic backbones, and thus usually exhibit low oral bioactivity due to poor absorption and short half lives due to rapid proteolysis. Therefore, there remains a need for improved MMP inhibitors.

SUMMARY OF THE INVENTION

This invention provides compounds having matrix metalloprotease inhibitory activity. These compounds are useful for inhibiting matrix metalloproteases and, therefore, combating conditions to which MMP's contribute. Accordingly, the present invention also provides pharmaceutical compositions and methods for treating such conditions.

The compounds described relate to a method of treating a mammal comprising administering to the mammal a matrix metalloprotease inhibiting amount of a compound according to the invention sufficient to:

(a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

(b) retard tumor metastasis or degenerative cartilage loss following traumatic joint injury;

(c) reduce coronary thrombosis from atherosclerotic plaque rupture; or (d) temporarily reduce fertility (i.e., act as a birth control agent).

The compounds of the present invention are also usefull scientific research tools for studying functions and mechanisms of action of matrix metalloproteases in both in vivo and in vitro systems. Because of their MMP-inhibiting activity, the present compounds can be used to modulate MMP action, thereby allowing the researcher to observe the effects of reduced MMP activity in the experimental biological system under study.

The compounds of this invention are of the following generalized formula:

$$(T)_xA—B—D—E—G \quad (L)$$

In the above generalized formula (L), $(T)_xA$ represents a substituted or unsubstituted aromatic 6-membered ring or heteroaromatic 5–6 membered ring containing 1–2 atoms of N, O, or S. T represents one or more substituent groups, the subscript x represents the number of such substituent groups, and A represents the aromatic or heteroaromatic ring, designated as the A ring or A unit. When N is employed in conjunction with either S or O in the A ring, these heteroatoms are separated by at least one carbon atom.

The substituent group(s) T are independently selected from the group consisting of halogen; alkyl; haloalkyl; alkenyl; alkynyl; —$(CH_2)_pQ$ in which p is 0 or an integer of 1–4; and -alkenyl-Q in which the alkenyl moiety comprises 2–4 carbons. Q in the latter two groups is selected from the group consisting of aryl, heteroaryl, —CN, —CHO, —$NO_2$, —$CO_2R^2$, —$OCOR^2$, —$SOR^3$, —$SO\ R_2^3$, —$CON(R^2)_2$, —$SO_2N(R^2)_2$, —$C(O)R^2$—, —$N(R^2)_2$, —$N(R^2)C(O)R^2$, —$NR^2CO_2R^3$, —$NR^2C(O)N(R^2)_2$, $OR^4$, $SR^4$, $R^2$ represents H, alkyl, aryl, heteroaryl, arylalkyl, or heteroaryl-alkyl; $R^3$ represents alkyl, aryl, heteroaryl, arylalkyl, or heteroaryl-alkyl; and $R^4$ represents H, alkyl, aryl, heteroaryl, arylalkyl, heteroaryl-alkyl, alkenyl, alkynyl, haloalkyl, acyl, or alkyleneoxy or polyalkyleneoxy terminated with H, alkyl, or phenyl. Unsaturation in a moiety which is attached to Q or which is part of Q is separated from any N, O, or S of Q by at least one carbon atom. The A ring may be unsubstituted or may carry up to 2 substituents T. Accordingly, the subscript x is 0, 1, or 2.

In the generalized formula (L), D represents

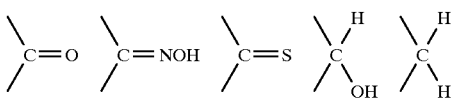

In the generalized formula (L), E represents the group

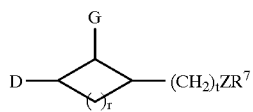

wherein r is 0–2, t is 0–4, Z represents —S—, —S(O)—, —$S(O)_2$—, —C(O)—, —$N(R^2)C(O)$—, —OC(O)—, or —O—, and $R^7$ is an optionally substituted amino, amide, carbamide, carbonic ester, as well as mono-, bi-, or tri-cyclic aromatic groups optionally substituted with a heteroatom selected from the group of N, O, and S. D and G in the structure above are the D and G units of general formula (L) and are not part of the E unit; they are included to demonstrate how the E unit is connected to the D and G units. When r=0 the structure above takes the form

In the generalized formula (L), G represents —$SO_3H$, —CN, —$PO_3H_2$, —M,

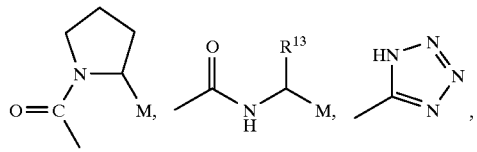

in which M represents —$CO_2H$, —$CON(R^{11})_2$, or —$CO_2R^{12}$, wherein $R^{11}$ represents H or alkyl of 1–4 carbons; and $R^{12}$ represents an alkyl of 1–4 carbons and $R^{13}$ represents any of the side chains of the 19 noncyclic naturally occurring amino acids.

Certain preferred embodiments include compounds having matrix metalloprotease inhibitory activity and the following generalized formula

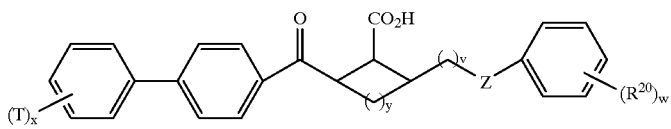

In the generalized formula (L), B represents an aromatic 6-membered ring or a heteroaromatic 5–6 membered ring containing 1–2 atoms of N, O, or S. It is referred to as the B ring or B unit. When N is employed in conjunction with either S or O in the B ring, these heteroatoms are separated by at least one carbon atom.

where v is 1–4, w is 0–3, y is 0–2, Z is selected from —S—, —S(O)—, —$S(O_2)$—, —C(O)—, —$N(R^2)C(O)$—, —OC (O)— OR —O— and each $R^{20}$ is independently H, alkyl, alkoxy, arylkoxy, halogen, —$COOR^2$, —$CON(R^2)_2$, $SOR^3$, $SO_2R^3$ or $COR^2$, wherein $R^2$ and $R^3$ are defined above. When y=0, the structure formed is a linear alkyl chain; when y=1 a four membered ring (cyclobutyl group) is formed; and when y=2 a five membered ring (cyclopentyl group) is formed. Preferably, the phenyl ring and $(R^{20})_w$ together (i.e., $R^7$) are one of the following:

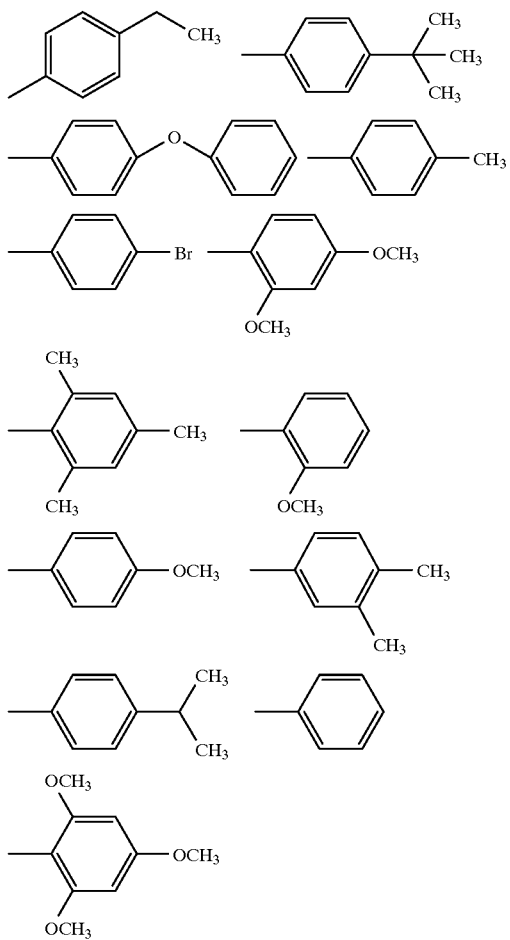

The invention also relates to certain intermediates useful in the synthesis of some of the claimed inhibitors. These intermediates are compounds having the generalized formula:

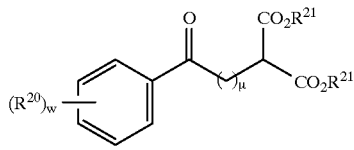

wherein $\mu$ represents v+1, i.e., $\mu$ is 1–5, and $R^{21}$ is $R^2$ as defined above or is an allylic substituent, and is preferably an allylic substituent.

The foregoing merely summarizes certain aspects of the present invention and is not intended, nor should it be construed, to limit the invention in any way. All of the patents and other publications recited in this specification are hereby incorporated by reference in their entirety.

DETAILED DESCRIPTION OF THE INVENTION

More particularly, the compounds of the present invention are materials having matrix metalloprotease inhibitory activity and the generalized formula:

$$(T)_x A—B—D—E—G \qquad (L)$$

in which $(T)_xA$ represents a substituted or unsubstituted aromatic or heteroaromatic moiety selected from the group consisting of

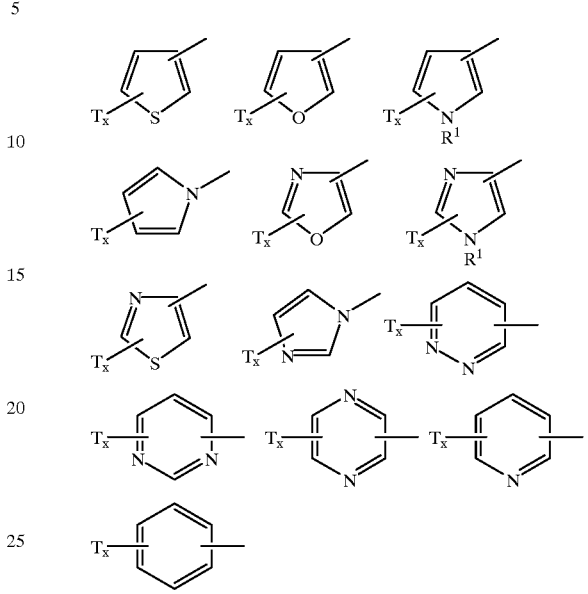

in which $R^1$ represents H or alkyl of 1–3 carbons. A may also represent an alkyl, aryl, heteroaryl, arylalkyl, alkoxyalkyl, hydroxyalkynyl, heteroaryl-alkyl, alkenyl, alkynyl, haloalkyl, acyl, alkyleneoxy, or polyalkyleneoxy each of which may be terminated with H, Et, allyl, alkyl, or phenyl.

Throughout this application, in the displayed chemical structures, an open bond indicates the point at which the structure joins to another group. For example,

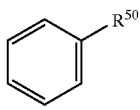

where $R^{50}$ is

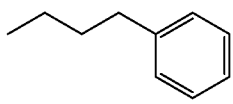

is the structure

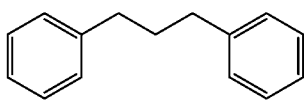

In these structures, the aromatic ring is referred to as the A ring or A unit, and each T represents a substituent group, referred to as a T group or T unit. Substituent groups T are independently selected from the group consisting of: the halogens —F, —Cl, —Br, and —I; alkyl of 1–10 carbons; haloalkyl of 1–10 carbons; alkenyl of 2–10 carbons; alkynyl of 2–10 carbons; —$(CH_2)_pQ$ in which p is 0 or an integer 1–4, and -alkenyl-Q in which the alkenyl moiety comprises 2–4 carbons. Q in each of the latter two groups is selected from the group consisting of aryl of 6–10 carbons; heteroaryl comprising 4–9 carbons and at least one N, O, or S heteroatom; —CN; —CHO; —NO$_2$; —CO$_2$R$^2$; —OCOR$^2$; —SOR$^3$; —SO$_2$R$^3$; —CON(R$^2$)$_2$; —SO$_2$N(R$^2$)$_2$; —C(O)R$^2$; —N(R$^2$)$_2$; —N(R$^2$)COR$^2$; —N(R$^2$)CO$_2$R$^3$; —N(R$^2$)CON(R$^2$)$_2$; —CHN$_4$; —OR$^4$; and —SR$^4$. The groups R$^2$, R$^3$, and R$^4$ are defined as follows:

R$^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R$^3$ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons.

R$^4$ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —(C$_q$H$_{2q}$O)$_r$R$^5$ in which q is 1–3, r is 1–3, and R$^5$ is H provided q is greater than 1, or R$^5$ is alkyl of 1–4 carbons, or phenyl; —(CH$_2$)$_s$X in which s is 2–3 and X is halogen; or —C(O)R$^2$.

Any unsaturation in a moiety which is attached to Q or which is part of Q is separated from any N, O, or S of Q by at least one carbon atom, and the number of substituents, designated x, is 0, 1, or 2.

The substituent group T can also be an acetylene containing moiety with the general formula:

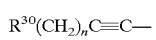

where n is 1–4 and R$^{30}$ is selected from the group consisting of: OH, MeO, N(n-Pr)$_2$, CH$_3$CO$_2$, CH$_3$CO$_2$OCO$_2$, CO$_2$H, CHO, Ph, 3-HO-Ph, and PhCHO, provided that when R$^{30}$ is Ph or 3-HO-Ph, n=0.

The B ring of generalized formula (L) is a substituted or unsubstituted aromatic or heteroaromatic ring, in which any substituents are groups which do not cause the molecule to fail to fit the active site of the target enzyme, or disrupt the relative conformations of the A and B rings, such that they would be detrimental. Such groups may be moieties such as lower alkyl, lower alkoxy, CN, NO$_2$, halogen, etc., but are not to be limited to such groups. B may also represent an alkyl, aryl, heteroaryl, arylalkyl, heteroaryl-alkyl, alkenyl, alkynyl, haloalkyl, acyl, alkyleneoxy or polyalkyleneoxy group.

In the generalized formula (L), B represents one of the following aromatic or heteroaromatic ring moieties:

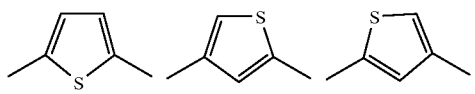

-continued

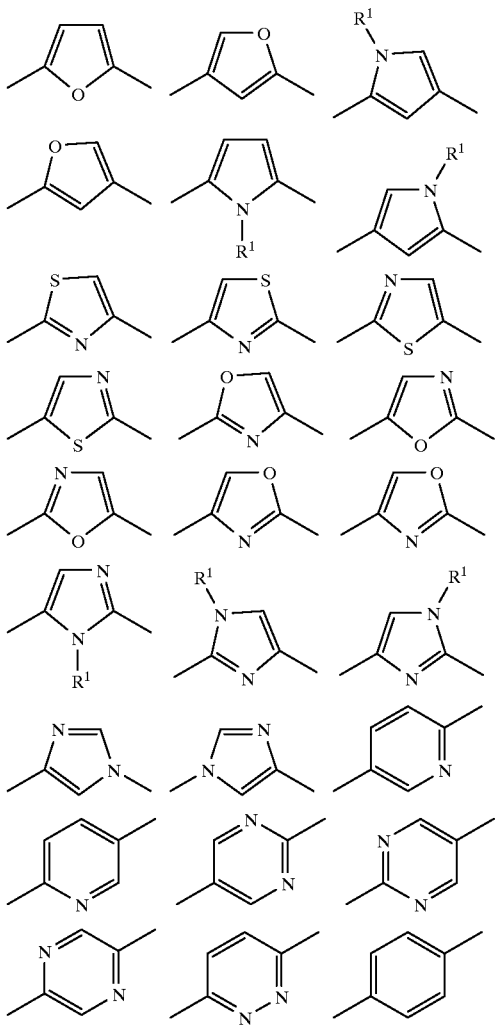

in which R$^1$ is defined as above. These rings are referred to as the B ring or B unit.

In the generalized formula (L), D represents one of the moieties

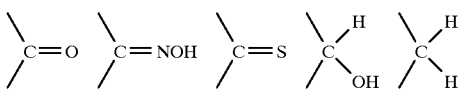

In the generalized formula (L), E represents the group

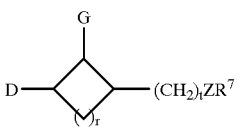

wherein r is 0–2, t is 0–4, Z represents —S—, —S(O)—, —S(O)$_2$—, —C(O)—, —N(R$^2$)C(O)—, —OC(O)—, or —O—, and R$^7$ is selected from the group consisting of alkyl of 1 to 12 carbons; aryl of 6 to 10 carbons; heteroaryl comprising 4 to 9 carbons and at least one N, O, or S heteroatom; arylalkyl in which the aryl portion contains 6 to 12 carbons and the alkyl portion contains 1 to 4 carbons; heteroarylalkyl in which the aryl portion contains 6 to 12 carbons and at least one N, O, or S heteroatom and the alkyl portion contains 1 to 4 carbons. In the above structure D and G are the D and G units of general formula (L) and are not part of the E unit; they are included to demonstrate how the E unit is connected to the D and G units. When r=0 the structure above takes the form

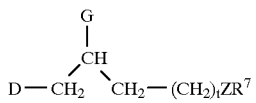

In addition, aryl or heteroaryl portions of any of the T or $R^7$ groups optionally may bear up to three substituents selected from the group consisting of —$(CH_2)_{y'}C(R^{11})(R^{12})$ OH, —$(CH_2)_{y'}OR^{11}$, —$(CH_2)_{y'}SR^{11}$, —$(CH_2)_{y'}S(O)R^{11}$, —$(CH_2)_{y'}S(O)_2R^{11}$, —$(CH_2)_{y'}SO_2N(R^{11})_2$, —$(CH_2)_{y'}N(R^{11})_2$, —$(CH_2)_{y'}N(R^{11})COR^{12}$, —$OC(R^{11})_2O$— in which both oxygen atoms are connected to the aryl ring, —$(CH_2)_{y'}OR^{11}$, —$(CH_2)_{y'}CON(R^{11})_2$, —$(CH_2)_{y'}CO_2R^{11}$, —$(CH_2)_{y'}OCOR^{11}$, -halogen, —CHO, —$CF_3$, —$NO_2$, —CN, and —$R^{12}$, in which y' is 0–4; $R^{11}$ represents H or alkyl of 1–4 carbons; and $R^{12}$ represents an alkyl of 1–4 carbons.

In particular embodiments, the optionally substituted $R^7$ group may be selected from one of the following:

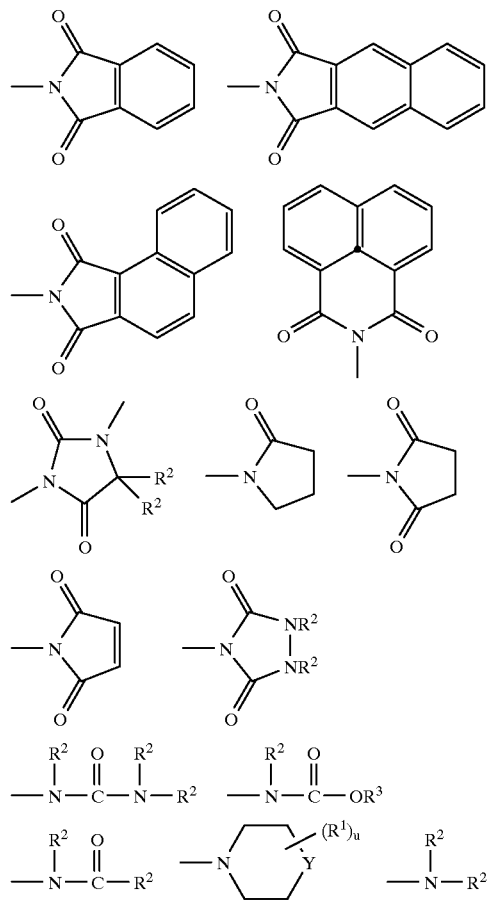

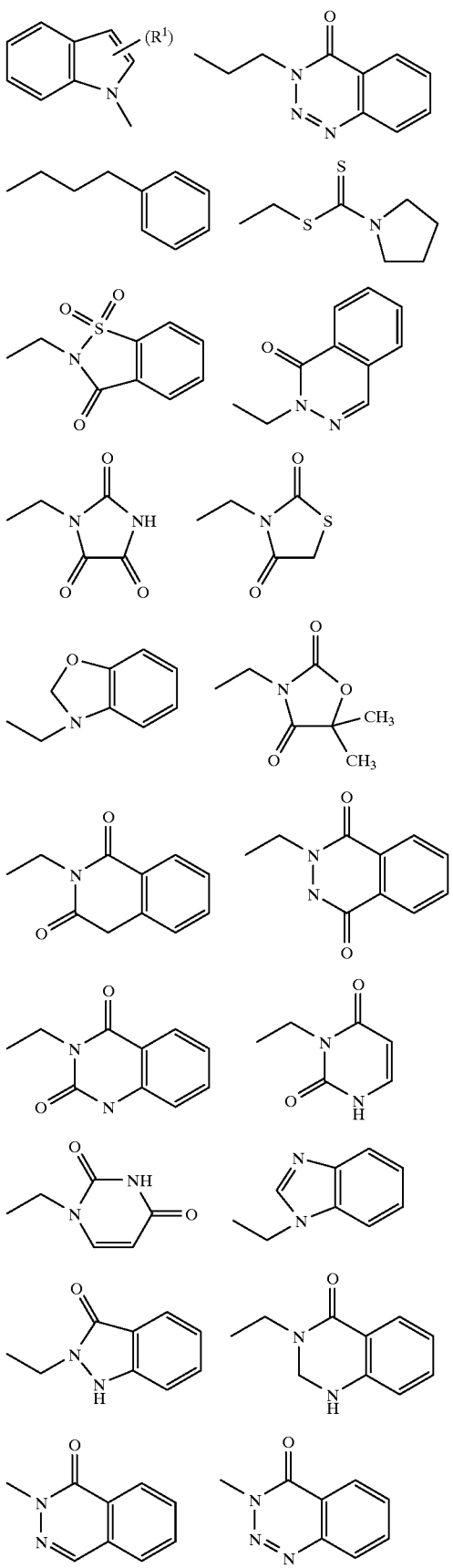

-continued

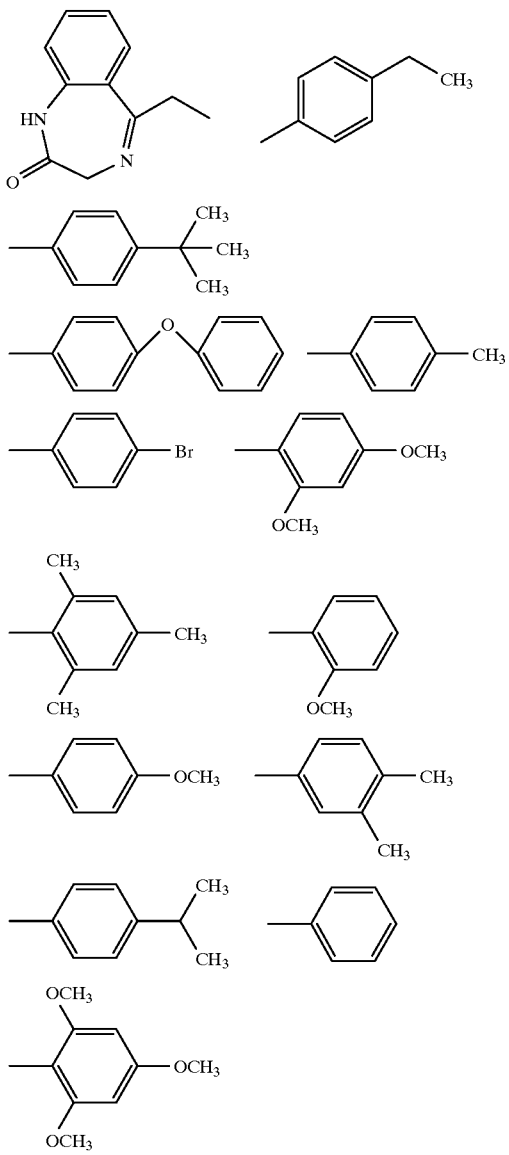

wherein u is 1–3 and $R^1$ is defined above.

In the generalized formula (L), G represents —$SO_3H$, —CN, —$PO_3H_2$, —M, or

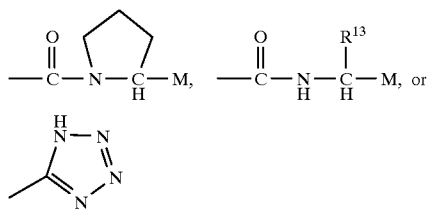

in which M represents —$CO_2H$, —$CON(R^{11})_2$, or —$CO_2R^{12}$, wherein $R^{11}$ and $R^{12}$ are defined above, and $R^{13}$ represents any of the side chains of the 19 noncyclic naturally occurring amino acids.

Pharmaceutically acceptable salts of the compounds falling within the generalized formula (L) are also within the invention.

The substituent group T is preferably halogen, or an ether $OR^4$ wherein $R^4$ is preferably alkyl of 1–12 carbons or arylalkyl in which the aryl portion is 6–10 carbons and the alkyl portion contains 1–4 carbons. Most preferably, T is halogen, and when T is $OR^4$, $R^4$ is alkyl of 1–6 carbons, or benzyl.

The subscript x, which defines the number of T substituents, is preferably 1 or 2, most preferably 1, and this substituent is on the 4-position of ring A.

It is to be understood that as used herein, the term "alkyl" means straight, branched, cyclic, and polycyclic materials. The term "haloalkyl" means partially or fully halogenated alkyl groups such as —$(CH_2)_2Cl$, —$CF_3$ and —$C_6F13$, for example.

In one of its embodiments, the invention relates to compounds of generalized formula (L) in which at least one of the units A, B, T, and E comprises a heteroaromatic ring. Preferred heteroaromatic ring-containing compounds are those in which the heteroaryl groups are heteroaryl of 4–9 carbons comprising a 5–6 membered heteroaromatic ring containing O, S, or $NR^1$ when the ring is 5-membered, and N when said ring is 6-membered. Particularly preferred heteroaromatic ring-containing compounds are those in which at least one of the A and B units comprises a thiophene ring. When A unit is thiophene, it is preferably connected to B unit at position 2 and carries one substituent group T on position 5. When B unit is thiophene, it is preferably connected through positions 2 and 5 to D and A units respectively.

In the generalized formula (L), the A and B rings are preferably phenyl and phenylene, respectively, the A ring preferably bears at least one substituent group T preferably located on the position furthest from the position of the A ring which is connected to the B ring, the D unit is preferably a carbonyl group, and preferably in the E unit r is 0, t is 1–4, Z is —CO—, and the optionally substituted $R^7$ group is one of the following

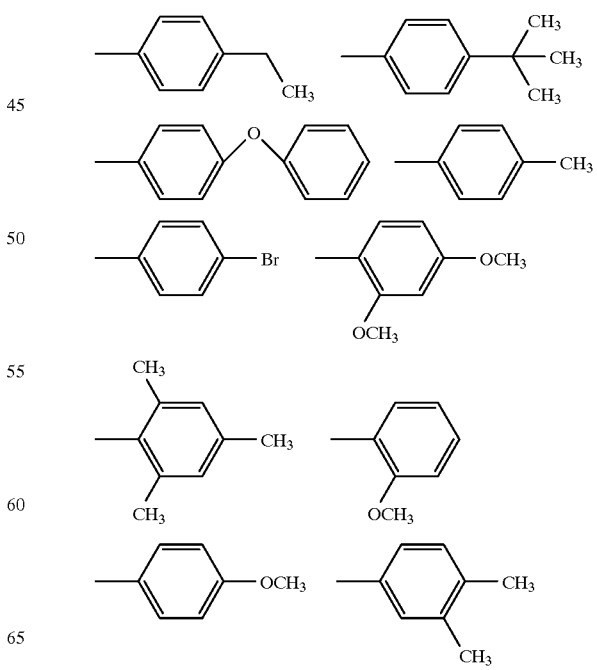

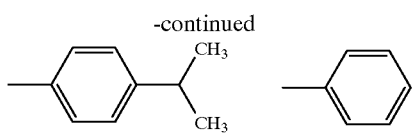

G is preferably carboxylic acid and attached to the E unit at the carbon beta to the D unit.

Particularly preferred embodiments are compounds having matrix metalloprotease inhibitory activity and the following generalized formula:

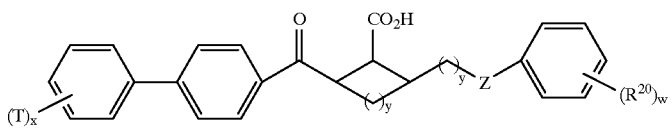

wherein v is 1–4, w is 0–3, y is 0–2, and each $R^{20}$ is independently alkyl of 1–5 carbons, alkoxy of 1–5 carbons, aryloxy, halogen, —$COOR^2$, —$C(O)N(R^2)_2$, $S(O)R^3$, $S(O)_2 R^3$ and $C(O)R^2$, wherein $R^2$ and $R^3$ are defined above. Most preferably, the phenyl ring and $(R^{20})_w$ together (i.e., $R^7$) are one of the following:

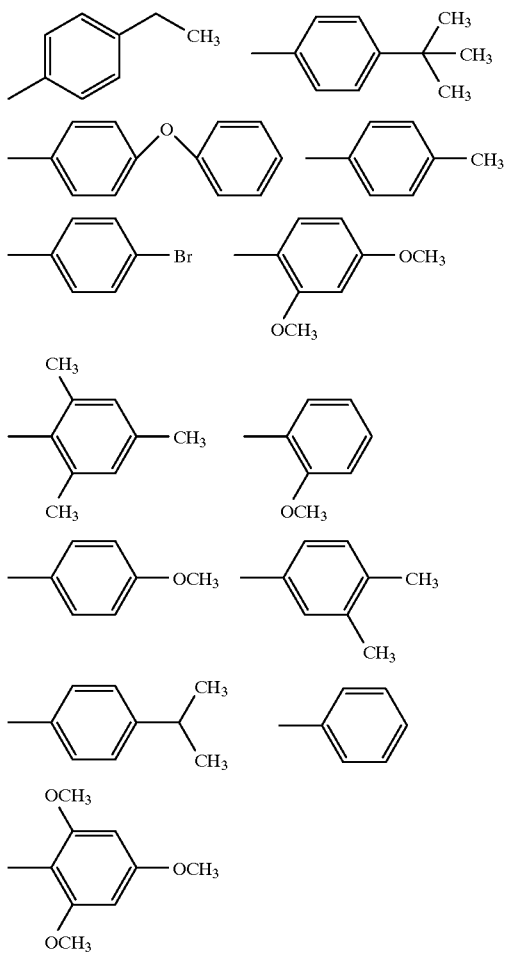

The invention also relates to certain intermediates useful in the synthesis of some of the claimed inhibitors. These intermediates are compounds having the generalized formula

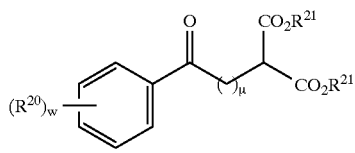

wherein $\mu$ is 1–5 and $R^{21}$ is $R^2$ or an allylic substituent, and is preferably an allylic substituent (designed Al1 in subsequent structures).

The most preferred compounds of the present invention are as indicated and named in the list below:

I) 4'-chloro-γ-oxo-α-(4-oxo-4-phenylbutyl)-[1,1'-biphenyl]-4-butanoic acid,
II) 4'-chloro-γ-oxo-α-(3-oxo-3-phenylpropyl)-[1,1'-biphenyl]-4-butanoic acid,
III) 4'-chloro-γ-oxo-α-(5-oxo-5-phenylpentyl)-[1,1'-biphenyl]-4-butanoic acid,
IV) 4'-chloro-γ-oxo-α-[6-oxo-6-phenyylhexyl)-[1,1'-biphenyl]-4-butanoic acid,
V) 4'-chloro-γ-oxo-α-[4-oxo4-(2,4,6-trimethoxyphenyl)butyl]-[1,1'-biphenyl]-4-butanoic acid,
VI) 4'-chloro-γ-oxo-α-[4-oxo-4-(2,4,6-trimethylphenyl)butyl]-[1,1'-biphenyl]-4-butanoic acid,
VII) 4'-chloro-γ-oxo-α-[4-oxo-4-(4-phenoxyphenyl)butyl]-[1,1'-biphenyl]-4-butanoic acid,
VIII) 4'-chloro-α-[4-(4-methylphenyl)-oxobutyl]-γ-oxo-[1,1'-biphenyl]-4-butanoic acid,
IX) α-[4-(4-bromophenyl)-4-oxobutyl]-4'-chloro-γ-oxo-[1,1'-biphenyl]-4-butanoic acid,
X) 4'-chloro-α-[4-(4-methoxyphenyl)-4-oxobutyl]-γ-oxo-[1,1'-biphenyl]-4-butanoic acid,
XI) 4'-chloro-α-[4-(3,4-dimethylphenyl)-4-oxobutyl]-γ-oxo-[1,1'-biphenyl]-4-butanoic acid,
XII) 4'-chloro-α-[4-(2,4-dimethoxyphenyl)-4-oxobutyl]-γ-oxo-[1,1'-biphenyl]-4-butanoic acid,
XIII) 4'-chloro-α-[4-[4-(1,1-dimethylethyl)phenyl]-4-oxobutyl]-γ-oxo-[1,1'-biphenyl]-4-butanoic acid,
XIV) 4'-chloro-α-[4-(4-ethylphenyl)-4-oxobutyl]-γ-oxo-[1,1'-biphenyl]-4-butanoic acid,
XV) 4'-chloro-α-[4-[4-(1-methylethyl)phenyl]-4-oxobutyl]-γ-oxo-[1,1'-biphenyl]-4-butanoic acid, and
XVI) 4'-clhoro-α-[4-(2-methoxyphenyl)-4-oxobutyl]-γ-oxo-[1,1'-biphenyl]-4-butanoic acid.

Those skilled in the art will appreciate that many of the compounds of the invention exist in enantiomeric or diastereomeric forms, and that it is understood by the art that such stereoisomers generally exhibit different activities in biological systems. This invention encompasses all possible stereoisomers which possess inhibitory activity against an MMP, regardless of their stereoisomeric designations, as well as mixtures of stereoisomers in which at least one member possesses inhibitory activity.

The compounds of the invention may be prepared by use of known chemical reactions and procedures. Nevertheless, the following general preparative methods are presented to aid one of skill in the art in synthesizing the inhibitors, with more detailed particular examples being presented below in the experimental section describing the working examples.

The compounds may be prepared as shown in Scheme I. Reaction of an ω-substituted-alkyl aryl ketone CI, in which the substituent X represents a leaving group, with a malonate ester CII in the presence of base affords the corresponding malonate, CIII. Appropriate leaving groups include, but are not limited to, halogens, phosphate esters, and sulfonate esters. Appropriate bases include, but are not limited to, hydroxide, alkoxide, or sodium hydride. Treatment of the substituted malonate, CIII, with substituted bromoacetophenone CIV in the presence of base affords disubstituted malonate, CV. Deprotection of malonate, CV, normally leads to diacid CVI, though in some cases, deprotection is followed with concommitant decarboxylation to the carboxylic acid, CVII. When necessary, decarboxylation is achieved by heating in a solvent, such as toluene or 1,4-dioxane.

The method used to deprotect diester CV is dependent on the moiety ($R^2$) to be removed. For example, deprotection of bis(allyl ester) CVIII may be acheived by treatment with a palladium catalyst in the presence of a suitable nucleophile, such as an amine, a malonate ester anion, or a hydride source, as shown in Scheme 2.

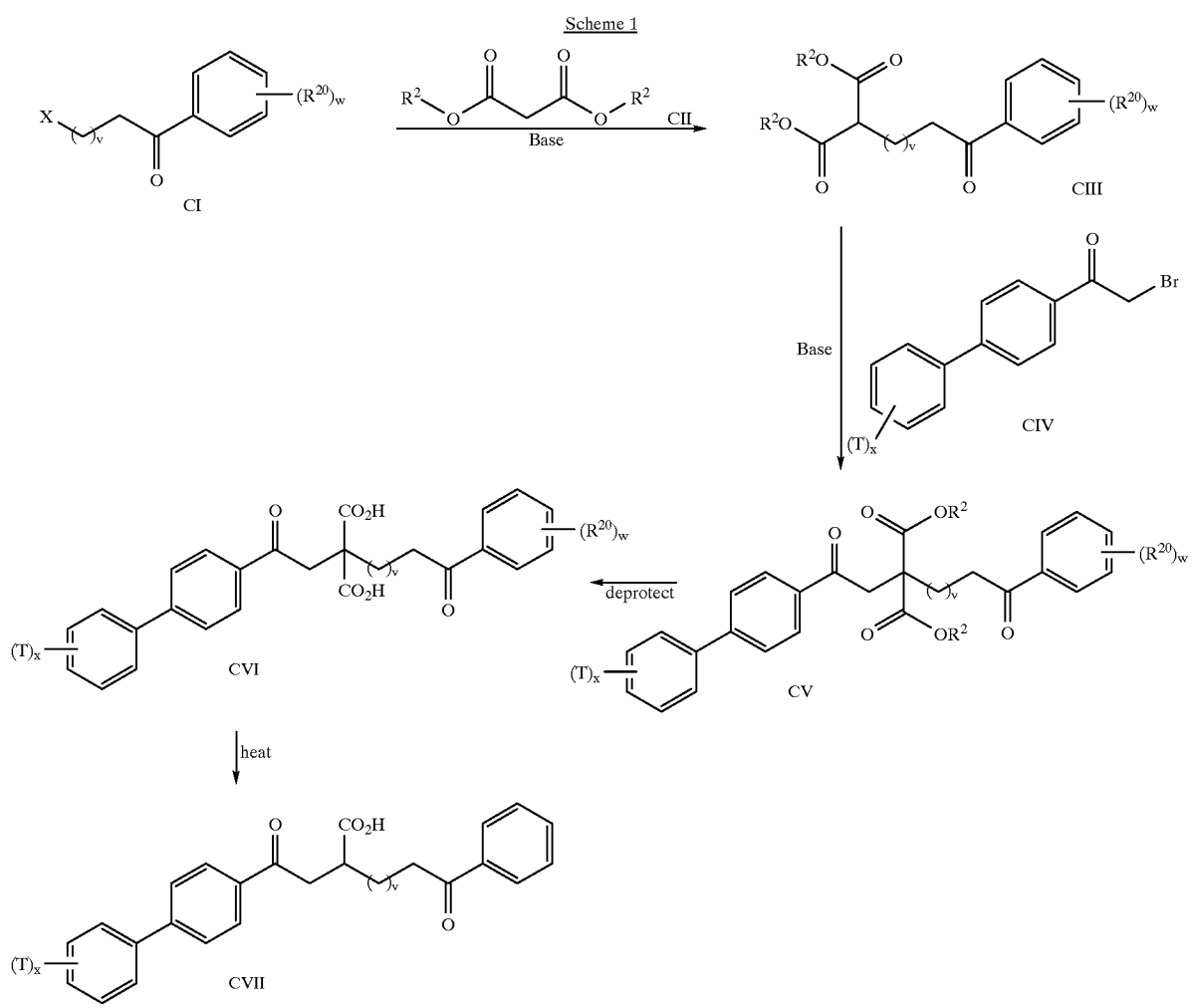

Scheme 1

Scheme 2

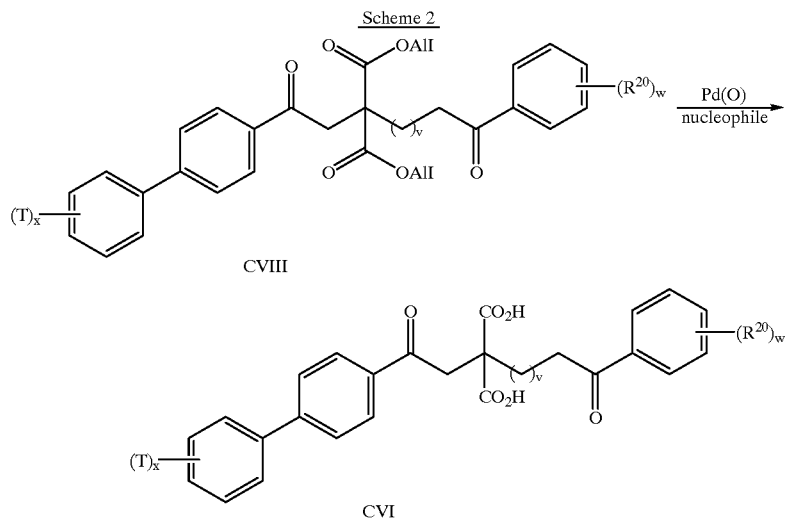

Many substituted ω-substituted-alkyl aryl ketones CI are commercially available, usually as the bromide or chloride. The ketones may be synthesized using any of a variety of approaches including those shown in Scheme 3. Friedel-rafts acylation of substituted aryl CIX with a haloacid (CX) affords desired ketone CI directly. Alternately, reaction of the haloacid halide CX with N,O-dimethylhydroxylamine generates the corresponding amide, which, when reacted with an aryl Grignard reagent or an aryllithium, CXIII, gives ketone CI. Lactones may be opened with aryl nucleophiles CXII to from the hydroxyketone CXV. Reaction of the hydroxyketone CXV with a halogenating source such as $PX_3$ or $SOCl_2$ then gives ketone CI. Hydroxyketone CXV may also be converted into the corresponding carboxylate or sulfonate ester. Interconversion of aryl ketones (CXVII and CI) may be achieved by displacement of the leaving group ($X^1$) with an appropriate nucleophile $X^2$. Optimally, this is done for $X^1$=Br, Cl under Finkelstein conditions.

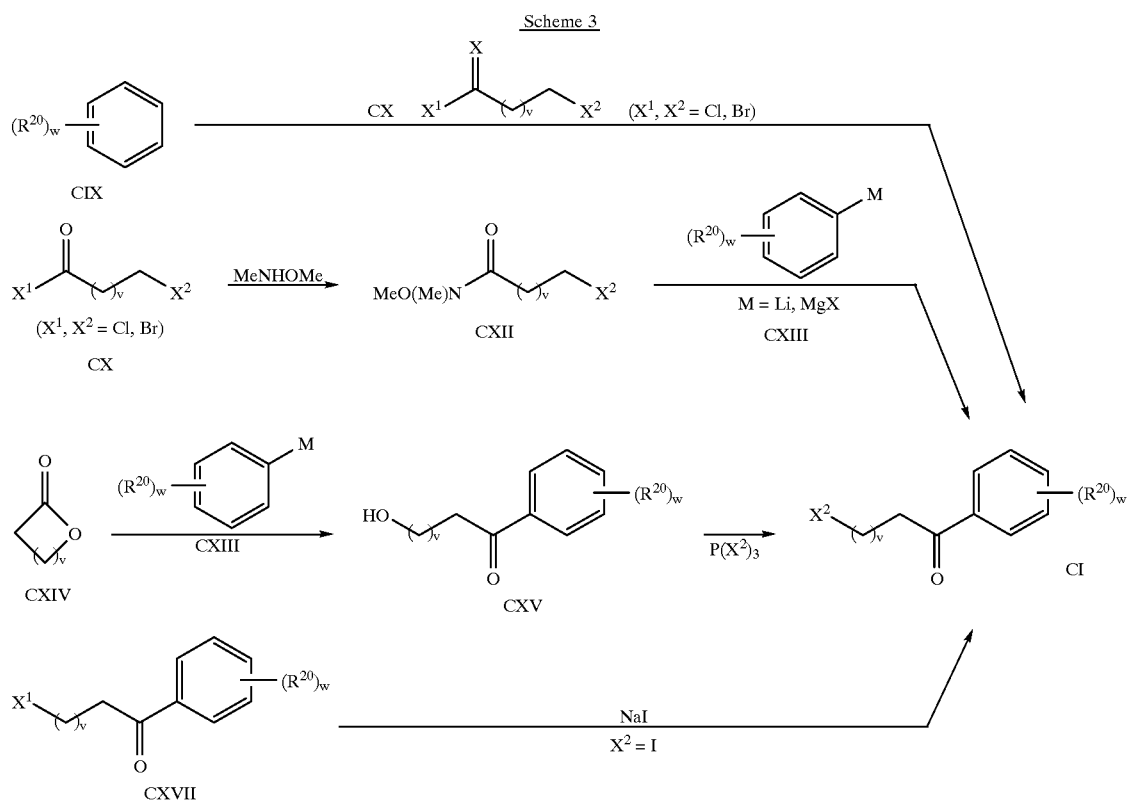

Suitable pharmaceutically acceptable salts of the compounds of the present invention include addition salts formed with organic or inorganic bases. The salt forming ion derived from such bases may be metal ions, e.g., aluminum, alkali metal ions, such as sodium of potassium, alkaline earth metal ions such as calcium or magnesium, or an amine salt ion, of which a number are known for this purpose. Examples include ammonium salts, arylalkylamines such as dibenzylamine and N,N-dibenzylethylenediamine, lower alkyl amines such as methylamine, t-butylamine, procaine, lower alkylpiperidines such as N-ethylpiperidine, cycloalkylamines such as cyclohexylamine or dicyclohexylamine, 1-adamantylamine, benzathine, or salts derived from amino acids like arginine, lysine or the like. The physiologically acceptable salts such as the sodium or potassium salts and the amino acid salts can be used medicinally as described below and are preferred.

These and other salts which are not necessarily physiologically acceptable are useful in isolating or purifying a product acceptable for the purposes described below. For example, the use of commercially available enantiomerically pure amines such as (+)-cinchonine in suitable solvents can yield salt crystals of a single enantiomer of the invention compounds, leaving the opposite enantiomer in solution in a process often referred to as "classical resolution." As one enantiomer of a given invention compound is usually substantially greater in physiological effect than its antipode, this active isomer can thus be found purified in either the crystals or the liquid phase. The salts are produced by reacting the acid form of the invention compound with an equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compounds of the present invention have been found to inhibit the matrix metalloproteases MMP-3, MMP-9 and MMP-2, and are therefore useful for treating or preventing the conditions referred to in the background section. As other MMPs not listed above share a high degree of homology with those listed above, especially in the catalytic site, it is deemed that compounds of the invention should also inhibit such other MMPs to varying degrees. Varying the substituents on the biaryl portions of the molecules, as well as those of the propanoic or butanoic acid chains of the claimed compounds, has been demonstrated to affect the relative inhibition of the listed MMPs. Thus compounds of this general class can be "tuned" by selecting specific substituents such that inhibition of specific MMP(s) associated with specific pathological conditions can be enhanced while leaving non-involved MMPs less affected.

The method of treating matrix metalloprotease-mediated conditions may be practiced in mammals, including humans, which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the inhibitors may be by any suitable mode known to those skilled in the art. Examples of suitable parenteral administration include intravenous, intra articular, subcutaneous and intramuscular routes. Intravenous administration can be used to obtain acute regulation of peak plasma concentrations of the drug. Improved half-life and targeting of the drug to the joint cavities may be aided by entrapment of the drug in liposomes. It may be possible to improve the selectivity of liposomal targeting to the joint cavities by incorporation of ligands into the outside of the liposomes that bind to synovial-specific macromolecules. Alternatively intramuscular, intra articular or subcutaneous depot injection with or without encapsulation of the drug into degradable microspheres e.g., comprising poly(DL-lactide-co-glycolide) may be used to obtain prolonged sustained drug release. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps with delivery of the drug through a cannula into the synovial spaces. Examples include the subcutaneously implanted osmotic pumps available from ALZA, such as the ALZET osmotic pump.

Nasal delivery may be achieved by incorporation of the drug into bioadhesive particulate carriers (<200 $\mu$m) such as those comprising cellulose, polyacrylate or polycarbophil, in conjunction with suitable absorption enhancers such as phospholipids or acylcarnitines. Available systems include those developed by DanBiosys and Scios Nova.

A noteworthy attribute of the compounds of the present invention in contrast to those of various peptidic compounds referenced in the background section of this application is the oral activity of the present compounds. Oral delivery may be achieved by incorporation of the drug into tablets, coated tablets, dragees, hard and soft gelatine capsules, solutions, emulsions or suspensions. Oral delivery may also be achieved by incorporation of the drug into enteric coated capsules designed to release the drug into the colon where digestive protease activity is low. Examples include the OROS-CT/Osmet™ and PULSINCAP™ systems from ALZA and Scherer Drug Delivery Systems respectively. Other systems use azo-cross linked polymers that are degraded by colon specific bacterial azoreductases, or pH sensitive polyacrylate polymers that are activated by the rise in pH at the colon. The above systems may be used in conjunction with a wide range of available absorption enhancers.

Rectal delivery may be achieved by incorporation of the drug into suppositories.

The compounds of this invention can be manufactured into the above listed formulations by the addition of various therapeutically inert, inorganic or organic carriers well known to those skilled in the art. Examples of these include, but are not limited to, lactose, corn starch or derivatives thereof, talc, vegetable oils, waxes, fats, polyols such as polyethylene glycol, water, saccharose, alcohols, glycerin and the like. Various preservatives, emulsifiers, dispersants, flavorants, wetting agents, antioxidants, sweeteners, colorants, stabilizers, salts, buffers and the like are also added, as required to assist in the stabilization of the formulation or to assist in increasing bioavailability of the active ingredient(s) or to yield a formulation of acceptable flavor or odor in the case of oral dosing.

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of target enzyme which must be inhibited in order to treat the condition.

The matrix metalloprotease inhibitors of the invention are useful not only for treatment of the physiological conditions discussed above, but are also useful in such activities as purification of metalloproteases and testing for matrix metalloprotease activity. Such activity testing can be both in vitro using natural or synthetic enzyme preparations or in vivo using, for example, animal models in which abnormal destructive enzyme levels are found spontaneously (use of genetically mutated or transgenic animals) or are induced by administration of exogenous agents or by surgery which disrupts joint stability.

The following examples are offered for illustrative purposes only and are not intended, nor should they be construed, to limit the invention in any way.

EXAMPLES

General Procedures:

All reactions were performed in flame-dried or oven-dried glassware under a positive pressure of dry argon and were stirred magnetically unless otherwise indicated. Sensitive liquids and solutions were transferred via syringe or cannula and introduced into reaction vessels through rubber septa. Unless otherwise stated concentration under reduced pressure refers to use of a Buchi rotary evaporator at approximately 15 mmHg. Bulb-to-bulb concentrations were conducted using an Aldrich Kugeirohr apparatus, and in these cases temperature refer to oven temperatures.

Materials:

Commercial grade reagents and solvents were used without further purification except that tetraydrofuran (THF) and 1,2-diethoxyethane (DME) were doubly distilled from potassium, diethyl ether was distilled from sodium benzophenone ketyl, and $CH_2Cl_2$ was distilled from CaH.

Chromatography:

Analytical thin-layer chromatography (TLC) was performed on Whatman® pre-coated glass-backed silica gel 60 A F-254 250 μm plates. Visualization of plates was effected by one of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating and (e) immersion of the plate in an acidic ethanol solution of 2,4dinitrophenylhydrazine followed by heating.

Column chromatography was performed using 230–400 mesh EM Science® silica gel. Rotary chromatography was performed using pre-cast $SiO_2$ plates Alltech® on a Harrison research Chromatotron.

Instrumentation:

Melting points (mp) were determined with a Thomas-Hoover melting point apparatus and are uncorrected.

Proton ($^1H$) nuclear magnetic resonance (NMR) spectra were measured with a General Electric GN-ONEGA 300 (300 MHz) spectrometer, with either $Me_4Si$ (δ 0.00) or residual protonated solvent ($CHCl_3$ δ 7.24) as a standard. Carbon ($^{13}C$) NMR spectra were measured with a General Electric GN-OMEGA 300 (75 MHz) spectrometer with solvent ($CDCl_3$ δ 77.0) as a standard. All of the compounds synthesized in the experiments below were analyzed by NMR, and the spectra were consistent with the proposed structures in each case.

Liquid-cesium secondary ion mass spectra (MS), an updated version of fast ion bombardment (FAB) were obtained using a Kratos Concept 1-H spectrometer. All examples described below were analyzed by low resolution mass spectrometry (LRMS), and many examples were analyzed using high resolution mass spectrometry (HRMS). The spectra were consistent with the proposed structures in each case.

General Comments:

For multi-step procedures, sequential steps are noted by numbers.

Examples 1–5

Preparation of Compounds I–V

Step 1. Diallyl malonate: To a solution of malonic acid (100 g, 0.96 mol) in allyl alcohol (250 mL) was added $H_2SO_4$ (0.25 mL) and the mixture was heated at 70° C. for 12 h. The resulting solution was concentrated to approximately 100 mL under reduced pressure and diluted with hexanes (500 mL). This solution was washed with a saturated $K_2CO_3$ solution (250 mL) and a saturated NaCl solution (250 mL), dried ($Na_2SO_4$) and concentrated under reduced pressure. The resulting oil was distilled to afford diallyl malonate (156 g, 88%) as a colorless oil: bp 85° C. (0.01 mmHg); $^1H$ NMR ($CDCl_3$) δ 3.40 (s, 2H), 4.60 (m, 4H), 5.20 (m, 2H), 5.30 (m, 2H), 5.85 (m, 2H); $^{13}C$ NMR ($CDCl_3$) δ 41.2, 68.5 (2C), 118.5 (2C), 131.3 (2C), 165.9 (2C). The resultant compound is illustrated below:

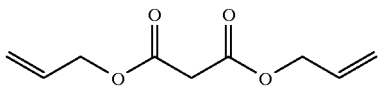

Step 2. 4Bromobutyrophenone: To a slurry of $AlCl_3$ (8.0 g, 0.60 mmol) in dry benzene (100 mL) at 0° C. was added 4-bromobutyryl chloride (5.8 mL). The resulting mixture was stirred at 0° C. for 2 h at which time TLC analysis indicated complete consumption of the acid chloride. The mixture was warmed to room temp., treated with an ice water mixture (100 mL), and concentrated under reduced pressure. The residue was separated between $CHCl_3$ (150 mL) and water (150 mL). The organic phase was washed with a saturated NaCl solution (150 mL), dried ($Na_2SO_4$), and concentrated under reduced pressure to give a light yellow oil (10.5 g, 92%) which was used without firther purification. The resultant compound is illustrated below:

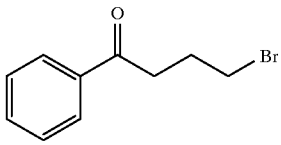

Step 3. Diallyl 2-(4-phenyl4-oxobutyl)malonate: To a slurry of NaH (60% in mineral oil, 0.21 g) in dry THF (35 mL) was added diallyl malonate (4.3 g, 25 mmol). The resulting slurry was stirred at room temp. for 30 min., then 4-bromobutyrophenone (4.6 g, 5.0 mmol) was added. This mixture was heated at the reflux temperature for 18 h, cooled to room temp., and acidified with a 1M $H_3PO_4$ solution (10 mL). The resulting mixture was extracted with $CH_2Cl_2$ (2×100 mL). The combined organic phases were sequentially washed with a 1M $H_3PO_4$ solution (100 mL), and a saturated NaCl solution (50 mL), dried ($MgSO_4$), and concentrated under reduced pressure (kugelrohr, 80° C., 4 mmHg) to give a crude oil which was firther purified using rotary chromatography ($SiO_2$, gradient from 1% EtOAc/hexane to 25% EtOAc/hexane) to give the desired malonate (2.1 g) as colorless oil containing a small amount of 4-bromobutyrophenone. The resultant compound (illustrated below) was used in the next step without further purification.

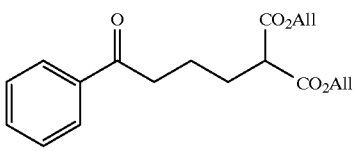

Step 4. Diallyl 2-(4-phenyl-4-oxobutyl)-2-(2-(4-(4-chlorophenyl)phenyl)-2-oxo)ethylmalonate: NaH (60% in mineral oil, 0.88 g, 2.2 mmol) was washed with hexanes (2×5 mL) then treated with a solution of diallyl 2-(4-phenyl-4-oxobutyl)malonate (0.74 g) in DME (5 mL) and the resulting mixture was stirred at room temp. for 30 min. The resulting slurry was treated with a solution of 1-(4-(4-chlorophenyl)phenyl)-2-bromoethan-1-one (0.60 g) and NaI (0.30 g) in DME (1.5 mL). The resulting mixture was stirred at room temp. overnight, then concentrated under reduced pressure. The residue was separated between $CH_2Cl_2$ (100 ml) and water (100 ml). The organic phase was dried ($MgSO_4$) and concentrated under reduced pressure to afford a brown oil, which was purified with rotary chromatography ($SiO_2$, gradient from 1% EtOAc/hexane to 50% EtOAc/hexane) to give the desired product as a colorless oil (0.72 g, 64%). The resultant compound is illustrated below:

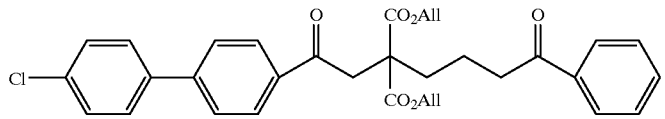

Step 5. 2-(4-Phenyl-4-oxobutyl)-2-(4-(4-chlorophenyl)phenyl)-2-oxoethyl)malonic acid: To a solution of diallyl 2-(4-phenyl-4-oxobutyl)-2-(2-(4-(4-chlorophenyl)phenyl)-2-oxoethyl)malonate (0.70 g) in 1,4-dioxane (12.5 mL) was added $Pd(PPh_3)_4$ (0.028 g) and pyrrolidine (120 μL), and the resulting solution was stirred at room temp. for 1 h at which time TLC (10% MeOH/$CH_2Cl_2$) indicated complete consumption of starting material. The resulting mixture was concentrated under reduced pressure. The residue was dissolved in EtOAc (25 mL), washed sequentially with water (25 mL) and a 1M $H_3PO_4$ (25 mL), dried ($MgSO_4$), and concentrated under reduced pressure to give an orange solid (0.51 g), which was recrystallized (EtOAc/hexane) to give a light tan solid (0.27 g, 45%), illustrated below:

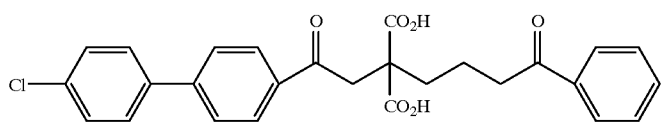

Step 6. 2-(2-(4-(4-chlorophenyl)phenyl)-2-oxoethyl)-6-phenyl-6-oxohexanoic acid: A solution of 2-(4-phenyl-4-oxobutyl)-2-(2-(4-(4-chlorophenyl)phenyl)-2-oxoethyl) malonic acid (0.26 g) in dioxane (55 mL) was heated at the reflux temperature overnight, then cooled to room temp. and concentrated under reduced pressure to give a brown oil, which was crystallized (EtOAc/hexane) to afford the desired product as a light yellow solid (0.11 g, 44%): TLC (10% MeOH/$CH_2Cl_2$) $R_f$ 0.56; $^1$H NMR (DMSO) δ 1.64–1.71 (m, 4H), 2.88–2.90 (m, 1H), 3.05–3.10 (m, 2H), 3.16 (dd, J=40, 18.0 Hz, 1H), 3.44 (dd, J=9.6, 18.0 Hz, 1H), 7.50–7.66 (m, 5H), 7.78–7.86 (m, 4H), 7.98 (dm, J=7.0 Hz, 2H), 8.07 (d, J=8.5 Hz, 2H), 12.2 (br s, 1H); $^{13}$C NMR (DMSO) δ 21.9 (2C), 31.6, 38.2 (2C), 127.4 (2C), 129.2 (4C), 129.3 (2C), 129.6 (2C), 133.6, 133.8, 136.0, 137.2, 138.2, 143.7, 176.7, 198.5, 200.3; LRMS m/z (% abundance) 435 (M$^+$+H, 100), 437 (38). The resultant compound is illustrated below:

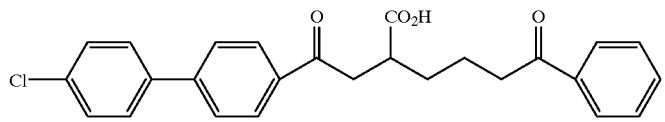

Other examples of the basic structure illustrated below which were synthesized in an analogous manner include:

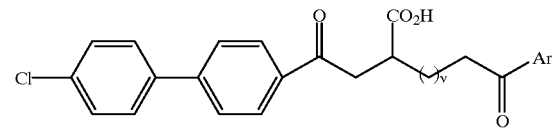

| Comp.# | Ar | v | TLC $(R_f)^a$ | Carbonyl $^{13}$C NMR(δ) |
|---|---|---|---|---|
| II | $C_6H_5$ | 1 | 0.43 | 177.2, 199.1, 200.5 |
| III | $C_6H_5$ | 3 | 0.54 | 176.7, 198.6, 200.5 |
| IV | $C_6H_5$ | 4 | 0.27$^b$ | 179.3, 197.8 (2C) |
| V | 2,4,6-$(CH_3O)_3C_6H_2$ | 2 | 0.49 | 180.6, 197.9, 204.4 |

$^a$TLC solvent system was 10% MeOH/$CH_2Cl_2$.
$^b$5% MeOH/$CH_2Cl_2$.

Examples 6 and 7

Preparation of Compounds VI and VII

Step 1 Diallyl 2-(4-(2,4,6-trimethylphenyl)-4-oxobutyl)malonate: To a slurry of NaH (60% in mineral oil, 0.36 g)

and NaI (0.55 g) in dry THF (37 mL) was added diallyl malonate (3.2 g, 18.5 mmol). The resulting slurry was stirred at room temp. for 30 min., then 4-bromo-1-(2,4,6-trimethylphenyl)-1-butanone (1.0 g, 3.7mmol) was added. This mixture was heated at the reflux temperature for 18 h, cooled to room temp., and acidified with a 1M $H_3PO_4$ solution (10 mL). The resulting mixture was extracted with $CH_2Cl_2$ (2×100 mL). The combined organic phases were sequentially washed with a 1M $H_3PO_4$ solution (100 mL), and a saturated NaCl solution (50 ml), dried ($MgSO_4$), and concentrated under reduced pressure (kugelrohr, 80° C., (4 mmHg)) to give a crude oil which was further purified using rotary chromatography ($SiO_2$, gradient from 1% EtOAc/hexane to 5% EtOAc/hexane) to give starting bromide (0.34 g) followed by the desired malonate (0.36 g). The resultant compound is illustrated below and was used in the next step without further purification as described in example 1 step 4.

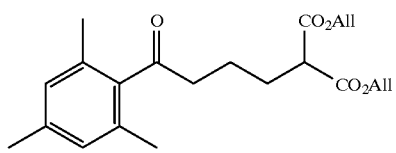

Examples of the following general structure were synthesized in an analogous manner include:

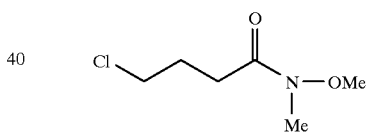

| Compound | Ar | v | TLC $(R_f)^a$ | Carbonyl $^{13}$C NMR($\delta$) |
|---|---|---|---|---|
| VI | 2,4,6-$(CH_3)_3C_6H_2$ | 2 | 0.57$^a$ | 176.6, 198.5, 210.2 |
| VII | 4-$(C_6H_5O)C_6H_4$ | 2 | 0.30$^b$ | 180.0, 197.7, 198.6 |

TLC solvent system was:
(a) 10% MeOH/$CH_2Cl_2$;
(b) 5% MeOH/$CH_2Cl_2$.

Examples 8–15

Preparation of Compounds VIII–XV

Step. 1. 4-Iodo-1-(4-methylphenyl)-1-butanone: A mixture of NaI (7.49 g) and 4-chloro-1-(4-methylphenyl)-1-butanone (4.9 g) in 2-butanone (25 mL) was heated at the reflux temperature for 18 h, cooled to room temp, and solids were removed by filtration. The filtrate was concentrated under reduced pressure and the residue was separated between hexane (250 mL) and water (250 mL). The organic phase was sequentially washed with a saturated $NaHSO_3$ solution (100 mL), and a saturated NaCl solution (100 mL), then dried ($MgSO_4$), and concentrated under reduced pressure to afford the desired product as an off-white solid (3.2 g, 44%). The resultant compound is illustrated below:

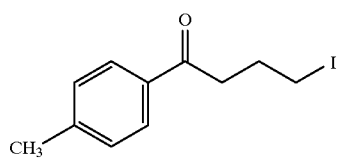

and was used in the next step without further purification as described in example 1 step 3.

Examples of the following general structure which were synthesized in an analogous manner include:

| Comp.# | Ar | v | TLC $(R_f)^a$ | Carbonyl $^{13}$C NMR($\delta$) |
|---|---|---|---|---|
| VIII | 4-$(CH_3)C_6H_4$ | 2 | 0.51 | 176.6, 198.5, 199.9 |
| IX | 4-$BrC_6H_4$ | 2 | 0.41 | 179.9, 198.0, 198.9 |
| X | 4-$(CH_3O)C_6H_4$ | 2 | 0.42 | 180.1, 197.8, 198.7 |
| XI | 3,4-$(CH_3)_2C_6H_3$ | 2 | 0.43 | 180.2, 198.0, 200.0 |
| XII | 2,4-$(CH_3O)_2C_6H_3$ | 2 | 0.32 | 180.1, 198.0, 200.2 |
| XIII | 4-$((CH_3)_3C)_3C_6H_4$ | 2 | 0.43 | 180.1, 197.8, 199.7 |
| XIV | 4-$(C_2H_5)_3C_6H_4$ | 2 | 0.49 | 179.2, 197.8, 199.7 |
| XV | 4-$((CH_3)_2CH)C_6H_4$ | 2 | 0.40 | 180.1, 197.8, 199.7 |

$^a$TLC solvent system was 10% MeOH/$CH_2Cl_2$.

Example 16

Preparation of Compound XVI

Step 1. N-Methyl-N-methoxy-4-chlorobutanamide: To a solution of N, O-dimethylhydroxyl-amine hydrochloride (9.8 g) in pyridine (250 mL) was added 4-chlorobutyryl chloride (5.6 mL) and the resulting mixture was stirred at room temp. for 3 d. The resulting mixture was concentrated under reduced pressure, dissolved in $CH_2Cl_2$, sequentially washed with a saturated $NaHCO_3$ solution (100 mL), water (100 mL), a 1M $H_3PO_4$ solution (100 mL), and a saturated NaCl solution (100 mL), dried ($MgSO_4$), and concentrated. The resulting orange oil was purified by rotary chromatography ($SiO_2$, gradient from 1% EtOAc/hexane to 50% EtOAc/hexane) to yield the desired product (illustrated below) as a yellow oil (2.7 g, 32%):

Step 2. 4-Chloro-1-(2-methoxyphenyl)-1-butanone: A mixture of Mg (2.3 g) and iodine (6 crystals) was flame dried under Ar to make a purple haze. This was cooled and THF (10 mL) was added, followed by a solution of 2-bromoanisole (3 mL) in THF (20 mL). When the initial reaction subsided, a solution of 2-bromoanisole (8.3 mL) in THF (30 mL) was added and the mixture was heated under reflux for 2 h and cooled to room temp.

To a mixture of N-methyl-N methoxy-4-chlorobutanamide (1.24 g) in THF (75 mL) at 0° C. was added the Grignard reagent (approximately 1.44M, 6.25 mL) and the reaction mixture was stirred at 0° C. for 3 d. After further reaction for 6 h at room temp., the reaction was quenched by the addition of a saturated $NH_4Cl$ solution (100 mL) and water (100 mL) and the phases were separated. The aqueous phase was extracted with $CH_2Cl_2$ (2×100 mL). The combined organic phases were washed with a saturated NaCl solution (100 mL), dried ($MgSO_4$) and concentrated under reduced pressure to afford an orange oil (1.24 g). The crude ketone was purified by rotary chromatography ($SiO_2$, gradient from 2% EtOAc/hexane to 10% EtOAc/hexane) to yield the desired product as a colorless oil (0.30 g, 19%). This was used in the next step without further purification as described in example 8 step 1. The resultant compound is illustrated below:

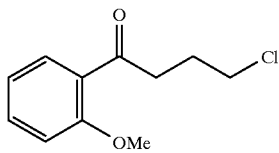

Examples of the following general structure which were synthesized in an analogous manner include:

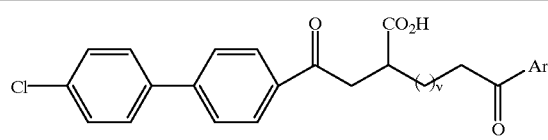

| Comp.# | Ar | v | TLC $(R_f)^a$ | Carbonyl $^{13}$C NMR($\delta$) |
|---|---|---|---|---|
| XVI | 2-$(CH_3O)C_6H_4$ | 1 | 0.34 | 176.8, 197.9, 202.5 |

TLC solvent system was 10% MeOH/$CH_2Cl_2$.

Example 17

Biological Assays of Invention Compounds
P218 Quenched Fluorescence Assay for MMP Inhibition:
The P218 quenched fluorescence assay (Microfluorometric Profiling Assay) is a modification of that originally described by Knight, et al., FEBS Lett. 296, 263, 1992 for a related substance and a variety of matrix metalloproteinases (MMPs) in cuvettes. The assay was run with each invention compound and the three MMPs, MMP-3, MMP-9 and MMP-2, analyzed in parallel, adapted as follows for a 96-well microtiter plate and a Hamilton AT® workstation.
P218 Fluorogenic Substrate: P218 is a synthetic substrate containing a 4-acetyl-7-methoxycoumarin (MCA) group in the N-terminal position and a 3-[2, 4-dinitrophenyl]-L-2,3-diaminopropionyl (DPA) group internally. This is a modification of a peptide reported by Knight (1992) that was used as a substrate for matrix metalloproteinases. Once the P218 peptide is cleaved (putative clip site at the Ala-Leu bond), the fluorescence of the MCA group can be detected on a fluorometer with excitation at 328 nm and emission at 393 nm. P218 is currently being produced by BACHEM Bioscience, Inc.exclusively for the Bayer Corporation. P218 has the structure:

H-MCA-Pro-Lys-Pro-Leu-Ala-Leu-DPA-Ala-Arg-NH2 (MW 1332.2)

Recombinant Human CHO Stromelysin (MMP-3)
Recombinant Human CHO Pro-MMP-3: Human CHO pro-stromelysin-257 (pro-MMP-3) was expressed and purified as described by Housley, et al., J. Biol. Chem. 268, 4481, 1993.
Activation of Pro-MMP-3: Pro-MMP-3 at 1.72 $\mu$M (100 $\mu$g/mL) in 5 mM Tris at pH 7.5, 5 mM $CaCl_2$, 25 mM NaCl, and 0.005% Brij-35 (MMP-3 activation buffer) was activated by incubation with TPCK (N-tosyl-(L)-phenylalanine chloromethyl ketone) trypsin (1:100 w/w to pro-MMP-3) at 25° C. for 30 min. The reaction was stopped by addition of soybean trypsin inhibitor (SBTI; 5:1 w/w to trypsin concentration). This activation protocol results in the formation of 45 kDa active MMP-3, which still contains the C-terminal portion of the enzyme.

Preparation of Human Recombinant Pro-Gelatinase A (MMP-2):
Recombinant Human Pro-MMP-2: Human pro-gelatinase A (pro-MMP-2) was prepared using a vaccinia expression system according to the method of Fridman, et al., J. Biol. Chem. 267, 15398, 1992.
Activation of Pro-MMP-2: Pro-MMP-2 at 252 mg/mL was diluted 1:5 to a final concentration of 50 $\mu$g/mL solution in 25 mM Tris at pH 7.5, 5 mM $CaCl_2$, 150 mM NaCl, and 0.005% Brij-35 (MMP-2 activation buffer). p-Aminophenylmercuric acetate (APMA) was prepared at 10 mM (3.5 mg/mL) in 0.05 NaOH. The APMA solution was added at 1/20 the reaction volume for a final AMPA concentration of 0.5 mM, and the enzyme was incubated at 37° C. for 30 min. Activated MMP-2 (15 mL) was dialyzed twice vs. 2 L of MMP-2 activation buffer (dialysis membranes were pre-treated with a solution consisting of 0.1% BSA in MMP-2 activation buffer for 1 min. followed by extensive $H_2O$ washing). The enzyme was concentrated on Centricon concentrators (concentrators were also pre-treated a solution consisting of 0.1% BSA in MMP-2 activation buffer for 1 min. followed by washing with $H_2O$, then MMP-2 activation buffer) with re-dilution followed by reconcentration repeated twice. The enzyme was diluted to 7.5 mL (0.5 times the original volune) with MMP-2 activation buffer.
Preparation of Human Recombinant Pro-Gelatinase B (MMP-9):
Recombinant Human Pro-MMP-9: Human pro-gelatinase B (pro-MMP-9) derived from U937 cDNA as described by Wilhelm, et al. J. Biol. Chem. 264, 17213, 1989 was expressed as the full-length form using a baculovirus protein expression system. The pro-enzyme was purified using methods previously described by Hibbs, et al. J. Biol. Chem. 260, 2493, 1984.
Activation of Pro-MMP-9: Pro-MMP-2 20 $\mu$g/mL in 50 mM Tris at pH 7.4, 10 mM $CaCl_2$, 150 mM NaCl, and 0.005% Brij-35 (MMP-9 activation buffer) was activated by incubation with 0.5 mM p-aminophenylmercuric acetate (APMA) for 3.5 h at 37° C. The enzyme was dialyzed against the same buffer to remove the APMA.
Instrumentation:
Hamiltion Microlab AT Plus: The MMP-Profiling Assay was performed robotically on a Hamilton MicroLab AT Plus®. The Hamilton was programmed to: (1) serially dilute up to 11 potential inhibitors automatically from a 2.5 mM stock in 100% DMSO; (2) distribute substrate followed by inhibitor into a 96 well Cytofluor plate; and (3) add a single enzyme to the plate with mixing to start the reaction. Subsequent plates for each additional enzyme were prepared automatically by beginning the program at the substrate addition point, remixing the diluted inhibitors and beginning the reaction by addition of enzyme. In this way, all MMP assays were done using the same inhibitor dilutions.
Millipore Cytofluor II: Following incubation, the plate was read on a Cytofluor II fluorometric plate reader with excitation at 340 nM and emission at 395 nM with the gain set at 80.
Buffers:
Microfluorometric Reaction Buffer (MRB): Dilution of test compounds, enzymes, and P218 substrate for the microfluorometric assay were made in microfluorometric reaction buffer consisting of 50 mM 2-(N-morpholino) ethanesulfonic acid (MES) at pH 6.5 with 10 mM $CaCl_2$, 150 mM NaCl, 0.005% Brij-35 and 1% DMSO.
Methods:
MMP Microfluorometric Profiling Assay. The assay was done with a final substrate concentration of 6 $\mu$M P218 and approximately 0.5 to 0.8 nM MMP with variable drug concentrations. The Hamilton was programmed to serially dilute up to 11 compounds from a 2.5 mM stock (100% DMSO) to 10× the final compounds concentrations in the assay. Initially, the instrument delivered various amounts of microfluorometric reaction buffer (MRB) to a 96 tube rack of 1 mL Marsh dilution tubes. The instrument then picked up 20 μL of inhibitor (2.5 mM) from the sample rack and mixes it with a buffer in row A of the Marsh rack, resulting in a 50 μM drug concentration. The inhibitors were then serially diluted to 10, 5, 1, 0.2, 0.05 and 0.01 μM. Position 1 on the sample rack contained only DMSO for the "enzyme-only" wells in the assay, which resulted in no inhibitor in column 1, rows A through H. The instrument then distributed 107 μL of P218 substrate (8.2 μM in MRB) to a single 96 well cytofluor microtiter plate. The instrument re-mixed and loads 14.5 μL of diluted compound from rows A to G in the Marsh rack to corresponding rows in the microtiter plate. (Row H represents the "background" row and 39.5 μL of MRB was delivered in placed of drug or enzyme). The reaction was started by adding 25 μL of the appropriate enzyme (at 5.86 times the final enzyme concentration) from a BSA treated reagent reservoir to each well, excluding Row H, the "background" row. (The enzyme reservoir was pre-treated with 1% BSA in 50 mM Tris, pH 7.5 containing 150 mM NaCl for 1 hour at room temp., followed by extensive $H_2O$ washing and drying at room temp.).

After addition and mixing of the enzyme, the plate was covered and incubated for 25 min. at 37° C. Additional enzymes were tested in the same manner by beginning the Hamilton program with the distribution of P218 substrate to the microtiter plate, followed by re-mixing and distribution of the drug from the same Marsh rack to the microtiter plate. The second (or third, etc.) MMP to be tested was then distributed from a reagent rack to the microtiter plate with mixing, prior to covering and incubation. This was repeated for all additional MMP's to be tested.

IC50 Determination in Microfluorometric Assay: Data generated on the Cytofluor II was copied from an exported ".CSV" file to a master Excel spreadsheet. Data from several different MMPs (one 96 well plate per MMP) were calculated simultaneously. The percent inhibition was determined for each drug concentration by comparing the amount of hydrolysis (fluorescence units generated over 25 minutes of hydrolysis) of wells containing compound with the "enzyme only" wells in column 1. Following subtraction of the background the percent inhibition was calculated as:

((Control values−Treated values)/Control values)×100

Percent inhibitions were determined for inhibitor concentrations of 5, 1, 0.5, 0.1, 0.02, 0.005 and 0.001 μM of drug. Linear regression analysis of percent inhibition versus log inhibitor concentration was used to obtain $IC_{50}$ values.

TABLE I

Profiling Assay Data for Certain Compounds of the Invention

| Compound | MMP-3 $IC_{50}$ (nM) | MMP-9 $IC_{50}$ (nM) | MMP-2 $IC_{50}$ (nM) |
|---|---|---|---|
| I | 65.0 | 65.7 | 9.97 |
| II | 96.0 | 127 | 9.60 |
| III | 61.1 | 52.4 | 7.52 |
| IV | 109 | 175 | 34.1 |
| V | 71.7 | 132 | 8.13 |
| VI | 39.6 | 1310 | 30.8 |
| VII | 367 | 65.7 | 131 |
| VIII | 69.1 | 108 | 19.0 |

TABLE I-continued

Profiling Assay Data for Certain Compounds of the Invention

| Compound | MMP-3 $IC_{50}$ (nM) | MMP-9 $IC_{50}$ (nM) | MMP-2 $IC_{50}$ (nM) |
|---|---|---|---|
| IX | 125 | 131 | 28.3 |
| X | 122 | 145 | 25.1 |
| XI | 104 | 105 | 48.3 |
| XII | 115 | 225 | 25.1 |
| XIII | 222 | 167 | 71.6 |
| XIV | 89 | 126 | 29.4 |
| XV | 130 | 133 | 35.7 |
| XVI | 48.2 | 152 | 26.2 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A matrix metalloprotease-inhibiting compound having the generalized formula:

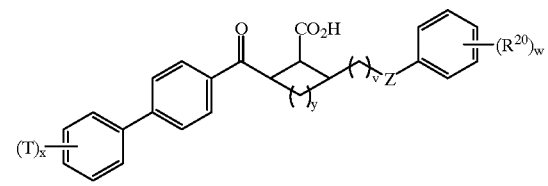

wherein
v is 1–4; y is 0–2 and when y=0 a linear alkyl chain results;
x is 0–2;
w is 0–3;
Z is a carbonyl group;
T is independently selected from the group consisting of
—F, —Cl, —Br, —I,
alkyl of 1–10 carbons,
haloalkyl of 1–10 carbons,
alkenyl of 2–10 carbons,
alkynyl of 2–10 carbons,
—$(CH_2)_pQ$ in which p is 0–4, and
-alkenyl-Q in which the alkenyl moiety comprises 2–4 carbons, and
Q is selected from the group consisting of
aryl of 6–10 carbons; heteroaryl comprising 4–9 carbons and at least one N, O, or S heteroatom; —CN; —CHO; —$NO_2$; —$CO_2R^2$; —$OCOR^2$; —$SOR^3$; —$SO_2R^3$; —$CON(R^2)_2$; —$SON(R^2)_2$; —$COR^2$; —$N(R^2)_2$; —$N(R^2)COR^2$; —$N(R^2)CO_2R^3$; $N(R^2)CON(R^2)_2$; —$CHN_4$; —$OR^4$; and
—$SR^4$; and each
$R^{20}$ is independently selected from the group consisting of H, alkyl of 1–5 carbons, alkoxy of 1–5 carbons, aryloxy, halogen, —$COOR^2$, —$CON(R^2)_2$, —$SOR^3$, —$SO_2R^3$, and $COR^2$;
$R^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons;

R³ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons; and R⁴ represents H; alkyl of 1–12 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; heteroaryl-alkyl in which the heteroaryl portion comprises 4–9 carbons and at least one N, O, or S heteroatom and the alkyl portion contains 1–4 carbons; alkenyl of 2–12 carbons; alkynyl of 2–12 carbons; —$(C_qH_{2q}O)_rR^5$ in which q is 1–3, r is 1–3, and R⁵ is H provided q is greater than 1, or R⁵ is alkyl of 1–4 carbons or phenyl; —$(CH_2)_sX$ in which s is 2–3 and X is halogen; or —$C(O)R^2$; and pharmaceutically acceptable salts thereof.

2. A matrix metalloprotease-inhibiting compound of claim 1 wherein T is Cl, x is 1, y is 0, v is 1–4, and

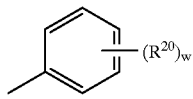

is selected from the group consisting of

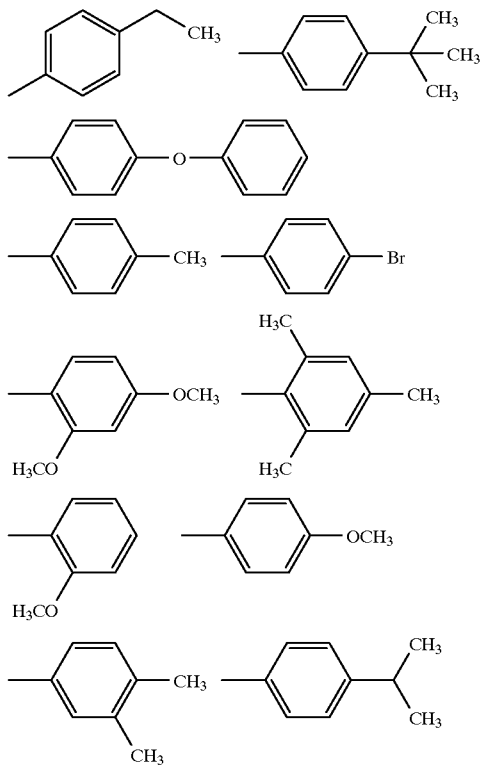

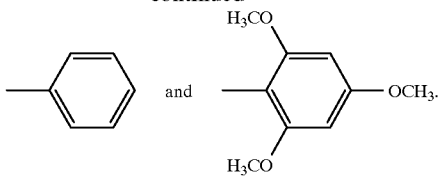

3. A method of inhibiting matrix metalloprotease activity comprising providing an effective matrix metalloprotease-inhibiting amount of a compound according to claim 1.

4. A method of inhibiting matrix metalloprotease activity comprising providing an effective matrix metalloprotease-inhibiting amount of a compound according to claim 2.

5. A pharmaceutical composition having matrix metalloprotease inhibitory activity, comprising a compound according to claim 1 and a pharmaceutically acceptable carrier.

6. A pharmaceutical composition having matrix metalloprotease inhibitory activity, comprising a compound according to claim 2 and a pharmaceutically acceptable carrier.

7. A method of treating a mammal comprising administering to the mammal a matrix metalloprotease inhibiting amount of a compound according to claim 1 sufficient to:

a) alleviate the effects of osteoarthritis, rheumatoid arthritis, septic arthritis, periodontal disease, corneal ulceration, proteinuria, aneurysmal aortic disease, dystrophobic epidermolysis, bullosa, conditions leading to inflammatory responses, osteopenias mediated by MMP activity, tempero mandibular joint disease, demyelating diseases of the nervous system;

b) retard tumor metastasis or degenerative cartilage loss following traumatic joint injury;

c) reduce coronary thrombosis from atherosclerotic plaque rupture; or d) effect birth control.

8. A method of treating a mammal comprising administering to the mammal a matrix metalloprotease inhibiting amount of a compound according to claim 2 sufficient to:

a) alleviate the effects of osteoarthritis, rheumatoid arthritis, septic arthritis, periodontal disease, corneal ulceration, proteinuria, aneurysmal aortic disease, dystrophobic epidernolysis, bullosa, conditions leading to inflammatory responses, osteopenias mediated by MMP activity, tempero mandibular joint disease, demyelating diseases of the nervous system;

b) retard tumor metastasis or degenerative cartilage loss following traumatic joint injury;

c) reduce coronary thrombosis from atherosclerotic plaque rupture; or d) effect birth control.

9. The method of claim 8 wherein said mammal is a human.

10. The method of claim 8 wherein the effect is alleviation of osteoarthritis.

11. The method of claim 8 wherein the effect is retardation of tumor metastasis.

12. A compound having the formula

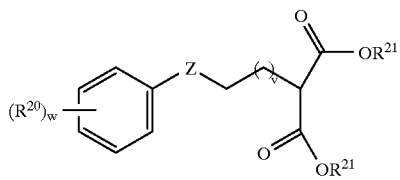

wherein v is 1–4;

w is 0–3;

Z is a carbonyl group;

each $R^{20}$ is independently H, alkyl of 1–5 carbons, alkoxy of 1–5 carbons, aryloxy, halogen, —COOR$^2$, —CON(R$^2$)$_2$, —SOR$^3$, —SO$_2$R$^3$, and COR$^2$; wherein $R^2$ represents H; alkyl of 1–6 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons; and $R^3$ represents alkyl of 1–4 carbons; aryl of 6–10 carbons; heteroaryl comprising 4–9 carbons and at least one N, O, or S heteroatom; arylalkyl in which the aryl portion contains 6–10 carbons and the alkyl portion contains 1–4 carbons; or heteroaryl-alkyl in which the heteroaryl portion comprises 4–9 carbons and at least one N, O, or S heteroatom and the alkyl portion contains 1–4 carbons; and $R^{21}$ represents $R^2$ or allyl.

* * * * *